US007635588B2

(12) United States Patent
King et al.

(10) Patent No.: US 7,635,588 B2
(45) Date of Patent: Dec. 22, 2009

(54) APPARATUS AND METHOD FOR DIFFERENTIATING MULTIPLE FLUORESCENCE SIGNALS BY EXCITATION WAVELENGTH

(75) Inventors: Howard G. King, Berkeley, CA (US); Steven J. Boege, San Mateo, CA (US); Eugene F. Young, Marietta, GA (US); Mark F. Oldham, Los Gatos, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 611 days.

(21) Appl. No.: 10/440,852

(22) Filed: May 19, 2003

(65) Prior Publication Data
US 2004/0014202 A1 Jan. 22, 2004

Related U.S. Application Data

(60) Provisional application No. 60/381,671, filed on May 17, 2002, provisional application No. 60/409,152, filed on Sep. 9, 2002, provisional application No. 60/450,734, filed on Feb. 28, 2003.

(51) Int. Cl.
*C12M 1/34* (2006.01)
*C12M 3/00* (2006.01)
*F21V 9/16* (2006.01)
*G01J 1/58* (2006.01)

(52) U.S. Cl. .................. 435/288.7; 435/808; 435/303.1; 435/288.4; 435/809; 250/459.1; 250/461.1; 250/461.2; 250/462.1; 250/483.1; 378/42; 378/45; 356/73

(58) Field of Classification Search .............. 435/288.7, 435/808, 303.1, 288.4, 809; 250/459.1, 461.1, 250/461.2, 462.1, 483.1; 378/45, 42; 356/73
See application file for complete search history.

(56) References Cited

U.S. PATENT DOCUMENTS 4,284,897 A  8/1981 Sawamura et al. ...... 250/461 B (Continued)

FOREIGN PATENT DOCUMENTS

EP  0 065 409 A2  11/1982

(Continued)

OTHER PUBLICATIONS

H.W. Sands Corp., *OLED Emitters Selected By Color Emission*, http://www.hwsands.com/productlists/oled/oled_emitters_color_emission.htm (Printed Jan. 10, 2003).
Hebner et al., *Local Tuning of Organic Light-Emitting Diode Color by Dye Droplet Application*, American Institute of Physics (1998).

(Continued)

*Primary Examiner*—William H Beisner
*Assistant Examiner*—Nathan A Bowers
(74) *Attorney, Agent, or Firm*—Leonnard D. Bowersox

(57) ABSTRACT

An apparatus and method are provided for differentiating multiple detectable signals by excitation wavelength. The apparatus can include a light source that can emit respective excitation light wavelengths or wavelength ranges towards a sample in a sample retaining region, for example, in a well. The sample can contain two or more detectable markers, for example, fluorescent dyes, each of which can be capable of generating increased detectable emissions when excited in the presence of a target component. The detectable markers can have excitation wavelength ranges and/or emission wavelength ranges that overlap with the ranges of the other detectable markers. A detector can be arranged for detecting an emission wavelength or wavelength range emitted from a first marker within the overlapping wavelength range of at least one of the other markers.

63 Claims, 8 Drawing Sheets

U.S. PATENT DOCUMENTS

| | | | |
|---|---|---|---|
| 4,626,684 A | 12/1986 | Landa | 250/328 |
| 4,643,877 A | 2/1987 | Opitz et al. | 422/68 |
| 4,673,289 A | 6/1987 | Gaucher | 356/72 |
| 4,683,202 A | 7/1987 | Mullins | 435/91 |
| 5,073,029 A | 12/1991 | Eberly et al. | 356/432 |
| 5,091,652 A | 2/1992 | Mathies et al. | 250/458.1 |
| 5,169,601 A | 12/1992 | Ohta et al. | 422/73 |
| 5,215,883 A | 6/1993 | Chu | 435/6 |
| 5,243,540 A | 9/1993 | Van Albert et al. | 364/500 |
| 5,256,880 A | 10/1993 | Loree et al. | 250/461.1 |
| 5,315,375 A | 5/1994 | Allen | 356/417 |
| 5,355,215 A | 10/1994 | Schroeder et al. | 356/317 |
| 5,371,016 A | 12/1994 | Berndt | 435/291 |
| 5,383,023 A | 1/1995 | Walleczek | 356/417 |
| 5,389,544 A | 2/1995 | Sugata et al. | 435/291 |
| 5,475,610 A | 12/1995 | Atwood et al. | 364/500 |
| 5,547,849 A | 8/1996 | Baer et al. | 435/7.24 |
| 5,567,947 A | 10/1996 | Kebabian | 250/458.1 |
| 5,595,708 A | 1/1997 | Berndt | 422/82.06 |
| 5,656,493 A | 8/1997 | Mullis et al. | 435/286.1 |
| 5,672,880 A | 9/1997 | Kain | 250/458.1 |
| 5,736,333 A | 4/1998 | Livak et al. | 435/6 |
| 5,759,781 A | 6/1998 | Ward et al. | 435/6 |
| 5,766,889 A | 6/1998 | Atwood | 435/91.2 |
| 5,779,978 A | 7/1998 | Hartmann et al. | 422/82.05 |
| 5,792,610 A | 8/1998 | Witney et al. | 435/6 |
| 5,846,842 A | 12/1998 | Herron et al. | 436/518 |
| 5,854,684 A | 12/1998 | Stabile et al. | 356/440 |
| 5,863,502 A | 1/1999 | Southgate et al. | 422/58 |
| 5,891,656 A * | 4/1999 | Zarling et al. | 435/7.92 |
| 5,926,271 A | 7/1999 | Couderc et al. | 356/318 |
| 5,928,907 A * | 7/1999 | Woudenberg et al. | 435/91.2 |
| 5,943,129 A | 8/1999 | Hoyt et al. | 356/318 |
| 6,040,940 A | 3/2000 | Kawasaki | 359/389 |
| 6,057,114 A | 5/2000 | Akong et al. | 435/7.21 |
| 6,096,272 A | 8/2000 | Clark et al. | 422/64 |
| 6,121,603 A * | 9/2000 | Hang et al. | 250/216 |
| 6,132,578 A | 10/2000 | Kambara et al. | |
| 6,197,575 B1 | 3/2001 | Griffith et al. | 435/288.4 |
| 6,287,871 B1 | 9/2001 | Herron et al. | 436/172 |
| 6,309,601 B1 | 10/2001 | Juncosa et al. | 422/68.1 |
| 6,331,438 B1 | 12/2001 | Aylott et al. | 436/172 |
| 6,337,740 B1 | 1/2002 | Parce | 356/344 |
| 6,352,672 B1 | 3/2002 | Mabile et al. | 422/82.08 |
| 6,355,934 B1 * | 3/2002 | Osgood et al. | 250/458.1 |
| 6,364,516 B1 | 4/2002 | Li et al. | 362/553 |
| 6,388,788 B1 | 5/2002 | Harris et al. | 359/196 |
| 6,411,835 B1 | 6/2002 | Modell et al. | 600/407 |
| 6,529,275 B2 | 3/2003 | Amirkhanian et al. | 356/413 |
| 6,958,464 B2 * | 10/2005 | Olszak et al. | 250/205 |
| 2002/0109100 A1 * | 8/2002 | Jackson et al. | 250/458.1 |
| 2002/0160535 A1 * | 10/2002 | Herron et al. | 436/518 |
| 2002/0185610 A1 * | 12/2002 | Stern | 250/458.1 |
| 2003/0160182 A1 * | 8/2003 | Petrich et al. | 250/458.1 |
| 2003/0230728 A1 * | 12/2003 | Dai et al. | 250/458.1 |

FOREIGN PATENT DOCUMENTS

| | | |
|---|---|---|
| EP | 0 640 828 A1 | 3/1995 |
| EP | 0 987 539 A1 | 3/2000 |
| JP | 07-120392 | 5/1995 |
| JP | 07-120393 | 5/1995 |
| JP | 07-174701 | 7/1995 |
| JP | 09-281078 | 10/1997 |
| WO | WO 97/46707 | 12/1997 |
| WO | WO 99/60381 | 11/1999 |
| WO | WO 00/13017 | 3/2000 |
| WO | WO 00/31518 | 6/2000 |
| WO | WO 00/58715 | 10/2000 |
| WO | WO 01/35079 A1 | 5/2001 |

OTHER PUBLICATIONS

Higuchi et al., *Kinetic PCR Analysis: Real-Time Monitoring Of DNA Amplification Reactions*, Bio Technology, vol. 11, pp. 1026-1030 (1993).

Hoyt, *Multiple Label Fluorescence Polarization Assay System and Method*, Publication No. US 2001/0033374 A1 (Oct. 25, 2001).

Kinjo, *Method of Analyzing A Target Nucleic Acid*, Publication No. 2002/0146688 A1 (Oct. 10, 2002).

Qiu et al., *Room Temperature Ultraviolet Emission From an Organic Light-Emitting Diode*, American Institute of Physics (2001).

Ririe et al., *Product Differentiation By Analysis of DNA Melting Curves During the Polymerase Chain Reaction*, Analytical Biochemistry, vol. 245, pp. 154-160 (1997).

Stumbo et al.,*Light Detection Device*, Publication No. US 2002/0060791 A1 (May 23, 2002).

Teresko, *Winning Technologies: Organic Light Emitting Diode*, Industry Week, (Dec. 11, 2000).

Tollefsrud, *Electronic Paper: Organic Light Emitting Diode*, http://komar.cs.stthomas.edu/qm425/01s/Tollefsrud2.htm (Printed Jan. 10, 2003).

Wittwer et al., *The LightCycler™ : A Microvolume Multisample Fluorimeter with Rapid Temperature Control*, BioTechniques vol. 22, No. 1, pp. 176-181 (Jan. 1997).

Notification of, and International Search Report, mailed Dec. 2, 2003, for International Application No. PCT/US03/15941.

* cited by examiner

|  | EXCITATION λ | |
|---|---|---|
|  | 470 | 525 |
| 5 FAM | 1.0 | 0.15 |
| TET | 0.1 | 1.0 |

APPARATUS AND METHOD FOR DIFFERENTIATING MULTIPLE FLUORESCENCE SIGNALS BY EXCITATION WAVELENGTH

CROSS-REFERENCE TO RELATED APPLICATIONS

The present application claims benefit under 35 U.S.C. § 119(e) from earlier filed U.S. Provisional Application No. 60/381,671, filed May 17, 2002, U.S. Provisional Application No. 60/409,152, filed Sep. 9, 2002, and U.S. Provisional Application No. 60/450,734, filed Feb. 28, 2003. All Patents, Patent Applications, and publications mentioned herein are incorporated herein in their entireties by reference.

BACKGROUND

For identification of biological and chemical sample compositions, various quenched or unquenched dyes can be added to a sample. An unquenched dye fluoresces at a particular emission wavelength when exposed to excitation light. Quenching dyes can greatly reduces the amount of light emitted by that dye at particular wavelengths.

The apparatus and methods currently in use for sample component detection are expensive, and can require a broad spectrum of light, multiple light sources, and/or multiple detectors, for recordation and interpretation of particular emitted wavelengths from a given sample. For example, in the past, the presence of the components in a sample has been determined by detecting and differentiating specific emission wavelengths emitted from a sample, requiring relatively expensive detectors for detecting and differentiating emission wavelengths. It is desirable to create a less expensive apparatus and method of determining the composition of a sample using fluorescent dyes.

SUMMARY

An apparatus and method for differentiating multiple fluorescence signals by excitation wavelength are set forth. The apparatus and method can allow for the determination of a sample composition using specific excitation wavelengths or wavelength ranges, a plurality of detectable markers, for example, fluorescent dyes, and one or more detectors. The advent of inexpensive light sources, such as, for example, light emitting diodes (LEDs), allows the apparatus and method of the present teaching to provide multiple excitation wavelengths or wavelength ranges at a low cost, and to economically and efficiently determine the presence or absence of target components of a sample composition.

According to various embodiments, the apparatus can include a sample well and a sample arranged in the sample well. The sample can include a plurality of components including a plurality of fluorescent dyes added thereto. Each of the plurality of fluorescent dyes can exhibit an excitation wavelength range and an emission wavelength range. The emission wavelength range can overlap with an emission wavelength range of one or more of the other fluorescent dyes.

According to various embodiments, an optical instrument can be provided that includes a light source arranged to emit an excitation wavelength or wavelength range toward a region capable of retaining a sample, such that a fluorescent dye, if present in the region, can be caused to fluoresce. The light source can provide excitation wavelength ranges that correspond to respective excitation wavelength ranges of a plurality of fluorescent dyes. A detector capable of detecting an emission wavelength emitted from a fluorescing dye can be used to determine the absence or presence of a component associated with the dye. For example, the dyes can include intercalating dyes, reporter dyes, free-floating dyes, and the like.

According to various embodiments, the light source of the apparatus can be an array of light generating sources, such as an array of LEDs, lasers, or both, for example. The apparatus can further include an excitation wavelength-excluding device, an excitation wavelength focusing device, or both.

According to various embodiments, one or more of the light source and the detector can be separated from the sample by a lightpipe.

According to various embodiments, a method of differentiating multiple fluorescent signals by excitation wavelength can be provided. The method can include providing a sample including a plurality of components in a sample well and adding a plurality of fluorescent dyes to the sample. Each of the plurality of fluorescent dyes can possess a respective excitation wavelength or wavelength range and an emission wavelength or wavelength range. A respective excitation wavelength range can be directed from a light source toward the sample to excite a fluorescent dye when in the presence of a target component. Emission wavelengths that are emitted from the fluorescent dye in the sample can be detected. The presence of a particular component in the sample can be determined by the detection of a corresponding emission wavelength. The method can then be repeated utilizing different excitation wavelengths to determine the presence of other particular components in the sample. Because excitation spectra are broad, a single excitation wavelength can excite multiple dyes simultaneously. Excitation wavelengths can be chosen so as excite a first dye more strongly compared to other dyes. The other dyes can be excited weakly compared to the first dye, or not at all in the presence of the respective excitation wavelength or wavelength range. The response of each possible dye versus excitation wavelength can be measured. The response of a sample of unknown constituents can be measured. Linear algebra techniques can be used to solve a system of linear equations. The solution set thus generated can describe the concentrations of the dyes in the sample of formerly unknown constituents.

According to various embodiments, a method of differentiating multiple fluorescent signals by excitation wavelength can include multiple light sources forming excitation beams in various excitation bands. The method can include a multi-notch filter. A plurality of overlapping multi-notch filters can be utilized in the method with at least one multi-notch filter being used as an excitation filter and at least one multi-notch filter being used as an emission filter.

BRIEF DESCRIPTION OF DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings:

FIGS. 6a-c depict several elements of various embodiments of the teachings, wherein FIG. 6a is a side view of a single sample well with a removed light source, FIG. 6b is a top view of a multiple sample well array depicting a light source and detection array, and FIG. 6c is a top view of an array of excitation wavelength excluding devices used with the light source and detection array of FIG. 6b;

It is to be understood that both the foregoing general description and the following detailed description are exemplary and explanatory only and are intended to provide a further explanation of the various embodiments of the present teachings.

DESCRIPTION

Figure 1:
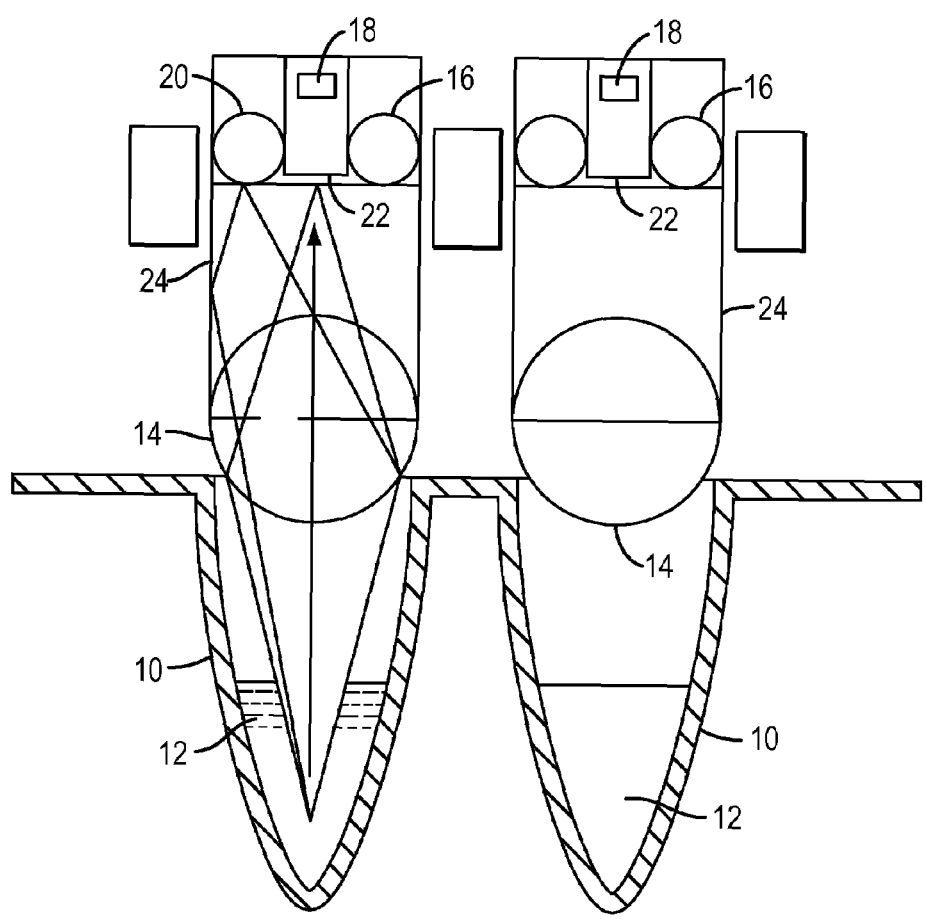
FIG. 1 depicts a side view of various embodiments.

According to various embodiments, for example, the embodiment shown in FIG. 1, an apparatus can include at least one sample well 10 adapted to receive a sample 12 containing at least two fluorescent dyes, a lens 14, a light source 16 capable of emitting at least two excitation wavelengths, and a detector 18 for detecting emission wavelengths. According to various embodiments, the apparatus can also include one or more excitation wavelength-excluding devices 22, one or more excitation wavelength-focusing devices, one or more lightpipes 24, one of more lenses 14, or combinations thereof.

According to various embodiments, the sample well 10 can be adapted to receive a sample 12 containing two or more components to be identified. For example, the sample 12 can be biological or chemical substances in solution, such as a sample containing DNA sequences for nucleic acid sequence amplification and/or sequencing detection. The sample 12 can be inserted into the sample well 10 directly, or the sample well 10 can be adapted to receive a sample container, for example, a cuvette or test tube. The sample well 10 can be a single sample well, or an array of sample wells arranged in a block, such as, for example, an array of 96 sample wells. Each sample well 10 can be heated and/or cooled during operation. Alternatively, the block can be capable of heating and cooling each sample well situated therein.

Figure 11:
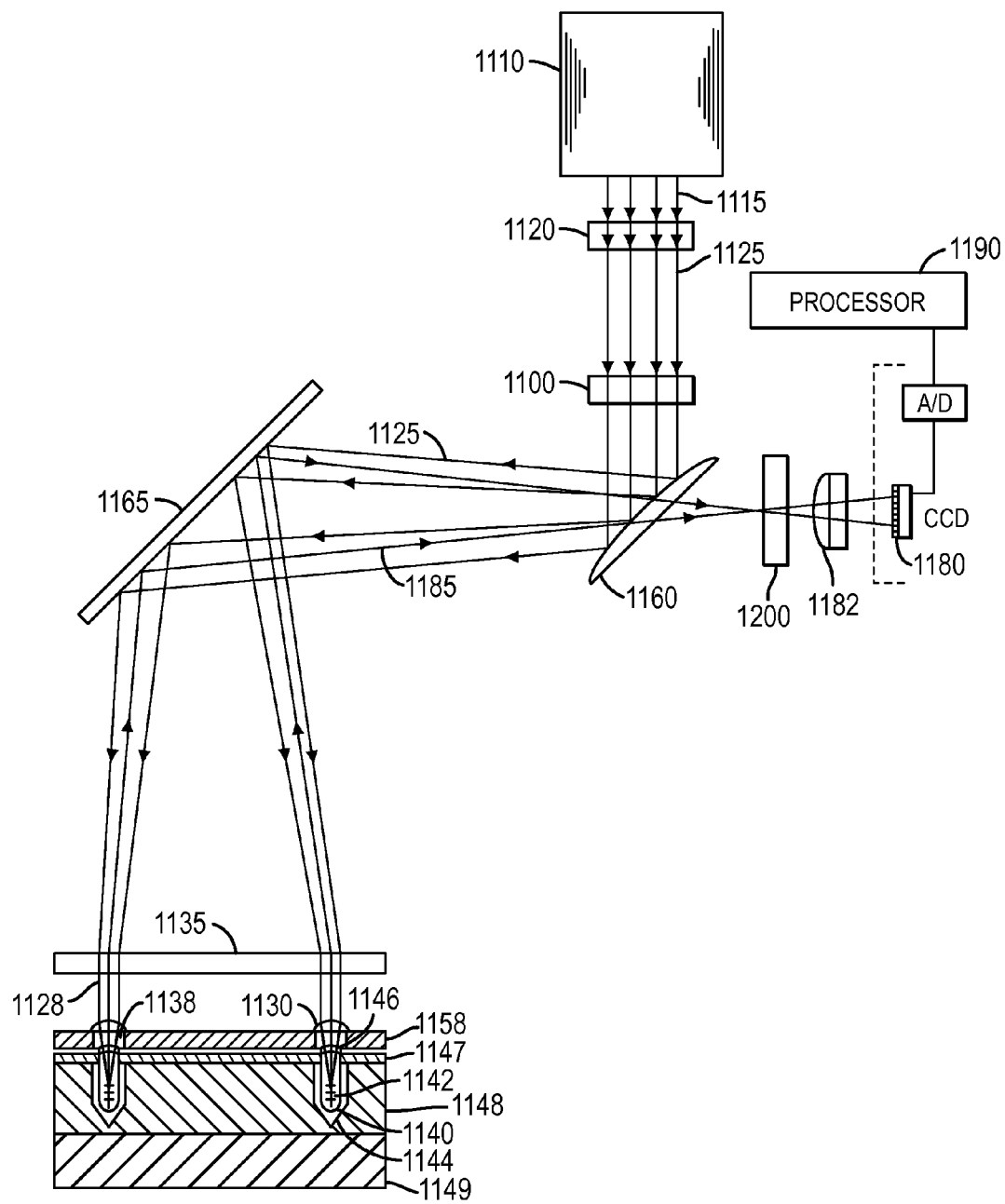
FIG. 11 is a schematic diagram of an optical instrument and an optical pathway generated by the instrument according to various embodiments.

FIG. 11 shows an exemplary instrument according to various embodiments that can include a reaction region holding assembly 1148, for example, a thermal cycler block, including wells 1144 for holding respective reaction regions 1140, for example, vials, spaced apart from one another. The reaction regions contain respective samples 1142. The samples can be, for example, respective suspensions of ingredients for polymerase chain reaction (PCR). If the reaction region holding assembly 1148 is a thermal cycler block, the assembly 1148 can include a thermal cycle controller 1149 for cycling the temperature of the block through a temperature program.

Each reaction 1140 can include, for example, any chamber, vessel, container, sample well, capsule, vial, sample array, centrifuge tube, or other containing, restraining, retaining, or confining device, without limitation, that is capable of retaining one or more samples for fluorometric analysis or illumination thereof. The reaction regions 1140 can be fixed, secured, mounted, or otherwise attached or connected to, separate from, or integral with, the reaction region holding assembly 1148. The assembly 1148 can be attached or connected to, or placed on, a surface of a substrate or a holder and positioned to enable one or more of the reaction regions to be illuminated by a light source. The holding assembly can be, for example, a purification tray, microtiter tray, multiwall tray, sample array, micro-well array of like device for holding multiple samples.

The samples 1142 to be analyzed can include aqueous suspensions of sample materials, for example, that might include a "seed" sample of a target nucleic acid sequence, selected primers, nucleic acids, enzymes, buffers, and other chemicals conventionally used for PCR, for an isothermal reaction or another DNA amplification method well known in the art.

The reaction regions 1140 can be heated and cooled in a predetermined cycle by electric heaters, liquid or air coolants, or a combination of these, or by other methods to achieve thermal cycling. The reaction regions 1140 can cycled between two temperature phases so as to affect PCR, for example.

According to various embodiments, two or more components of the sample 12 can be identified by adding a number of fluorescent dyes to the sample 12. Each component can be positively identified by the fluorescence of a dye.

According to various embodiments, each fluorescent dye can be selected so as to become unquenched due to the presence of a particular target component in the sample. Each fluorescent dye can be selected to possess particular excitation and emission wavelength ranges. After the dye has been added to the sample 12, a wavelength of light corresponding to the excitation wavelength range of the dye can be directed at the sample 12 by the light source 16, causing the dye to fluoresce when in the presence of a target component. The fluorescing dye can emit light at an emission wavelength that can be detected by a detector 18. Accordingly, the presence of the particular component in the sample 12 can be determined by detecting whether an emission beam at a particular wavelength or wavelength range is emitted from the sample 12 when a corresponding excitation beam is directed to the sample.

Figure 2:
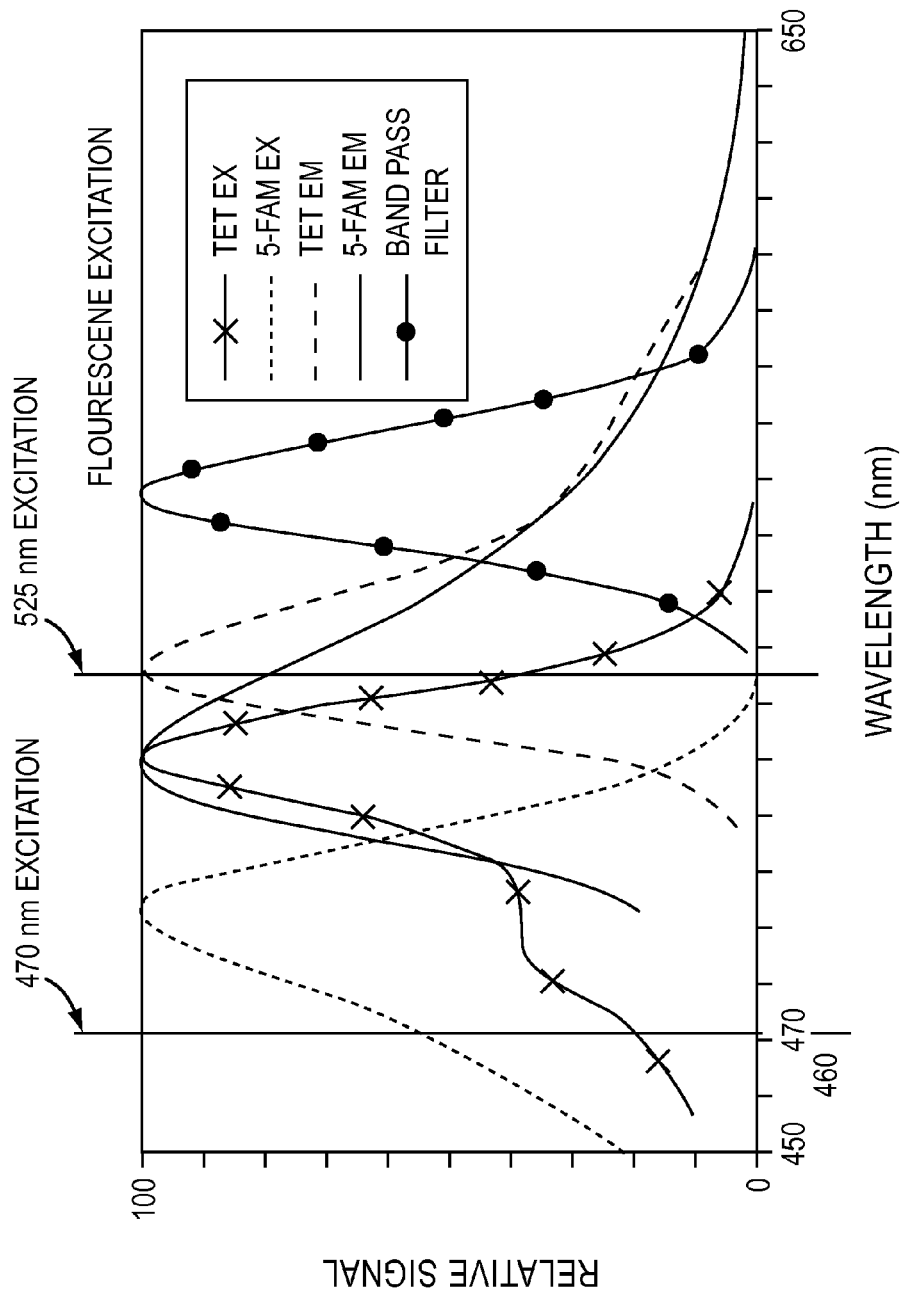
FIG. 2 is a graph showing the excitation and emission frequencies of two dyes, and the frequency of a bandpass filter for use in various embodiments.
Figures 3, 4:
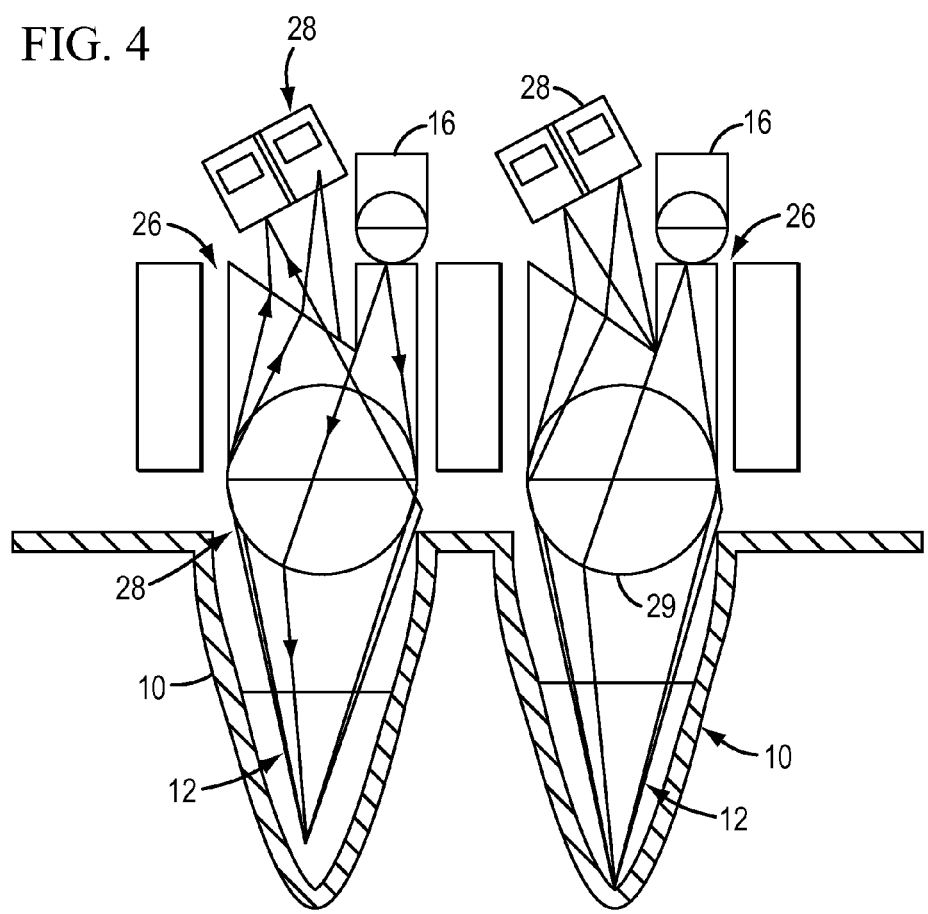
FIG. 3 is a table showing the relative amount of excitation of two dyes at two separate wavelength ranges.
FIG. 4 depicts an embodiment including a light source directed through a prism.

According to various embodiments, the presence of various dyes in a sample utilizing respective excitation wavelength ranges can be used to identify the various components. The plurality of fluorescent dyes can be chosen such that each dye possesses (a) a discrete or substantially discrete excitation wavelength range, and (b) an emission wavelength range that overlaps with an emission wavelength range of one or more of the other fluorescent dyes. For example, the excitation and emission wavelengths of exemplary dyes 5-FAM™ and TET™ are depicted in FIGS. 2 and 3. As shown, 5-FAM™ and TET™ possess substantially discrete excitation wavelength ranges centered at 470 nm and 525 nm, respectively. Moreover, referring to FIG. 2, within the wavelength range of approximately >600 nm, 5-FAM™ and TET™ possess substantially overlapping emission wavelengths. FIG. 2 depicts the emissions of the dyes using the following representation: TET Ex as a solid-line with x's through the line; 5-FAM Ex as a dashed-line using small dashes; TET Em as a dashed-line using long dashes; 5-FAM Em as a solid-line; and emissions after bandpass filter processing with o's through the line According to various embodiments, PCR dyes can be used that only fluoresce when bound to a target molecule. Nucleic acid sequence amplification dyes can also be attached to probes that also are connected to quenchers, and the action of nucleic acid sequence amplification enzymes will disassemble the dye-probe-quencher molecule causing the dye to increase its fluorescence. Nucleic acid sequence amplification can be performed using a variety of methods, for example, polymerase chain reaction (PCR), isothermal amplification reaction, well known in the art. When a PCR procedure is used, for example, the number of unquenched dye molecules doubles with every thermal cycle. Fluorescing dyes are well known in the art, and any of a plurality of fluorescent dyes having various excitation wavelengths can be used. Examples of such dyes include, but are not limited to, Rhodamine, Fluoroscein, dye derivatives of Rhodamine, dye derivatives of Fluoroscein, 5-FAM™, 6-carboxyfluorescein (6-FAM™), VIC™, hexachloro-fluorescein (HEX™), tetrachloro-fluorescein (TET™), ROX™, and TAMRA™. Dyes or other identifiers that can be used include, but are not limited to, fluorophores and phosphorescent dyes. Dyes can be used in combinations of two, three, four, or more dyes per sample. According to various embodiments, the family of 5-FAM™, 6-FAM™, VIC™, TET™, and/or ROX™ dyes can be used to indicate the presence of sample components.

According to various embodiments, there are a number of dyes that can be used in nucleic acid sequence amplification detection. The detection can be real-time. Some dyes weave themselves into the DNA and increase their fluorescence once they do. For these intercalating dyes, the fluorescence strength grows as the number of DNA molecules grows. This intercalation does not have to be sequence specific. Samples can be differentiated by looking at the DNA melting temperature. More commonly, a dye can be attached to one end of a probe DNA sequence and a quencher can be attached to the other end. When the probe binds to a target sequence, an enzyme can cleave the probe into pieces, unbinding the quencher and dye so the dyes can be excited and can release their energy via fluorescence rather than having it absorbed by the quencher. According to various embodiments, free-floating dyes can be used.

According to various embodiments, various detectable markers can be used, in addition or in alternate, to dyes. Markers can include, for example, fluorescing dyes, free-floating dyes, reporter dyes, probe dyes, intercalating dyes, and molecular beacons. Dyes that fluoresce when integrated into DNA can be intercalating dyes. Other dyes known as "reporter" dyes can attached to the ends of "probes" that have "quenchers" on the other end. A nucleic acid sequence amplification reaction, for example, PCR, can result in the disassembly of the Dye-Probe-Quencher molecule, so the reporter dye can emit an increased amount of fluorescence. Reporter dyes are not attached in any way to the sample. Free floating dyes can be floating freely in solution. Other fluorescing markers well know in the art can be utilized. According to various embodiments, molecular beacons can be single-stranded molecules with hairpins that preferentially hybridize with an amplified target to unfold.

As shown in FIGS. 1, 5, 6a, and 7, a detector 18 can be used to detect whether an emission wavelength is emitted from the sample 12. The detector can be any suitable device known in the art, including, for example, a photodiode, a charge coupled device (CCD), a camera, a CMOS detector, or any combination thereof. The detector can be adapted to relay information to a data collection device for storage, correlation, and/or manipulation of data, for example, a computer, a signal processing system.

Figure 8:
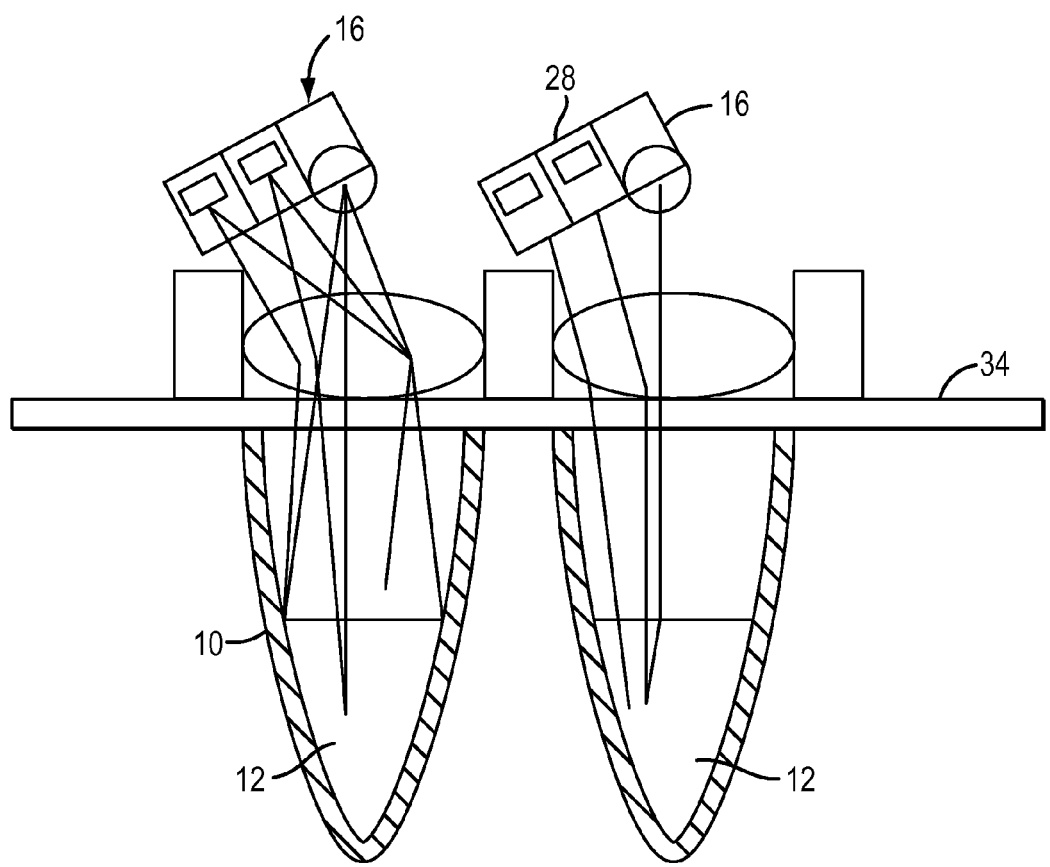
FIG. 8 depicts various embodiments wherein a light source, multiple detectors for each sample well, and a grating is used to separate the emission beam according to various wavelengths per grating diffraction.

Multiple emission detectors 28, as shown, for example, in FIGS. 4 and 8, each set to receive a respective range of wavelengths of light corresponding to the emission wavelength of particular dyes, can also be used to detect any emitted light. According to various embodiments, the multiple emission detectors 28 can be arranged as an array. Various types of multiple emission detectors for use according to various embodiments are described, for example, in Publication No. WO 01/69211 A1, which is incorporated herein in its entirety by reference.

According to various embodiments, the lens 14 can be a focusing lens that can focus a wavelength of light emitted from a light source 16 into the sample well 10. According to various embodiments, the lens 14 can focus the emission wavelength light into a detector 18, as shown, for example, in FIGS. 1, 6a, and 7.

The lens can be any suitable lens configuration, including one or more lenses. The lens can be any lens known to practitioners in the art, for example, a Fresnel lens or prism. A prism 26, as shown, for example, in FIG. 4, can be used in conjunction with a second lens 29. The prism 26 can be arranged to direct the light of the excitation beam into the sample well 10, and the second lens 29 can be arranged to focus the light of the emission beam into a detector or a detector array 28, as shown, for example, in FIG. 4. According to various embodiments, a prism 26 can be used independently without any additional lenses. According to various embodiments, articles known in the art can be arranged to direct the light, for example, a prism, a grating, a mask, of the excitation beam and/or emission beam.

According to various embodiments, the apparatus can include a light source, detector and a single lens, and can be substantially free of other optical components, for example, mirrors, beamsplitters, additional focusing lenses, etc. According to various embodiments, the apparatus does not include a lens. According to various embodiments, the distance between the light source and sample, and the distance between the sample and detector can be proportional or thereabout to the relative distances illustrated in FIG. 5. According to various embodiments, the light source can be spaced above the sample in the range from D/2 to 5D from the top surface of the sample, where D is the depth of the sample in the well.

Figure 5:
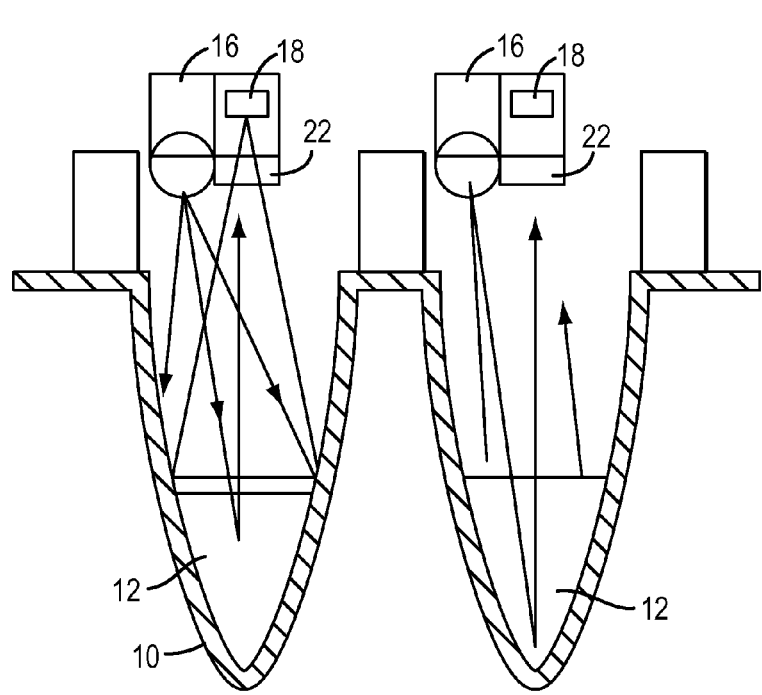
FIG. 5 depicts another embodiment of the present teachings.
Figure 6A:
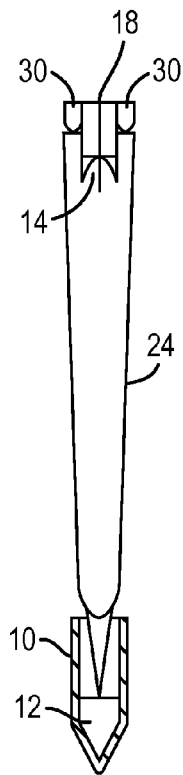
Figure 6B:
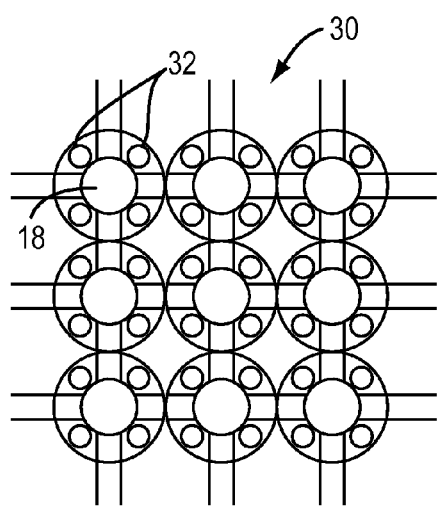

According to various embodiments, the light source 16 can include a source of light that can emit one or more respective wavelengths or wavelength ranges of light, for example, as shown in FIGS. 4 and 5, or an array 30 of two or more light sources 32, for example, as shown in FIGS. 1, 6a, and 6b.

According to various embodiments, a light array 30 includes two, three, four, or more sources of light 32 as shown, for example, in FIGS. 1, 6a and 6b. Each source of light 32 can emit a respective wavelength range of light to cause fluorescence of a different fluorescent dye. The sources of light 32 can each include any suitable light emitting device or devices that emit a narrow wavelength of light, for example, a LED, a laser, a solid state laser, a laser diode, or any combination thereof. If a laser light source is used, it can be scanned in one or more dimensions. Super bright LEDs can be used because they are inexpensive and can be arranged in a light array at low cost. According to various embodiments, separate LEDs or a packaged set of LEDs can be used in an array. Other suitable light sources will be apparent to practitioners in the art. According to various embodiments, the light source can include a combination of two, three, or more LEDs, laser diodes, and the like, such as, for example, an LED emitting at about 475 nm, an LED emitting at about 539 nm, and a photodiode emitting at about 593 nm.

According to various embodiments, the light emitted from the light source 16, such as an LED or a laser, can be divided between two samples, three samples, four samples, or more, reducing the number of light sources needed per sample well array. An exemplary multiple sample wells layout is shown, for example, in FIG. 7. The light can be divided between two or more sample wells 10 by any known device, including, for example, one or more fiber optics, flood illumination device, one more lens with or without a mask, and/or one or more beam splitter.

According to various embodiments, a broad-spectrum light source, for example, a white light or halogen light can be used as the light source 16. According to various embodiments, the emitted light of the broad-spectrum light source can be separated into distinct wavelengths or wavelength ranges such that one wavelength or wavelength range at a time can be directed toward the sample 12. The light can be divided into distinct wavelengths or wavelength ranges by an excitation wavelength focusing device, such as, for example, a prism (shown at 26 in FIG. 4), a diffraction grating (shown at 34 in FIG. 8), or a filter. The direction of a single wavelength or wavelength range can be controlled by use of an excitation wavelength-focusing device, such as, for example, a diffraction grating or filter. According to various embodiments, the broad spectrum light source can be filtered by way of a lowpass filter, for example, to prevent light in the range of emission wavelengths from reaching the sample. According to various embodiments, a pair of matching multi-notch filters can be used to prevent light in the range of emission wavelengths from reaching the sample.

According to various embodiments, the apparatus can include an excitation wavelength-excluding device 22, as shown in FIG. 1, for example. The excitation wavelength-excluding device 22 can include, for example, a diffraction grating, filter, prism, or mirror. The excitation wavelength-excluding device 22 can be positioned between the detector 18 and the sample well 10. For example, according to various embodiments, the excitation wavelength-excluding device 22 can be positioned immediately before and adjacent to a detector 18 as shown, for example, in FIGS. 1 and 7. According to various embodiments, the excitation wavelength-excluding device 22 can be a longpass filter which can transmit wavelengths greater than about 600 nm to ensure that substantially only the fluorescence emission wavelengths are received by the detector or detector array. The excitation wavelength-excluding device can be positioned between a detector and a lens, or between a lens and a sample as shown, for example, as a diffraction grating 34, in FIG. 8.

Figure 6C:
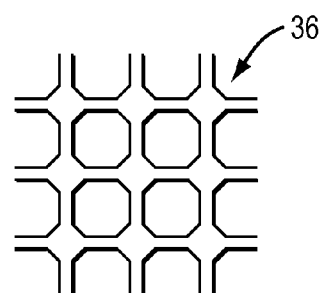
Figure 7:
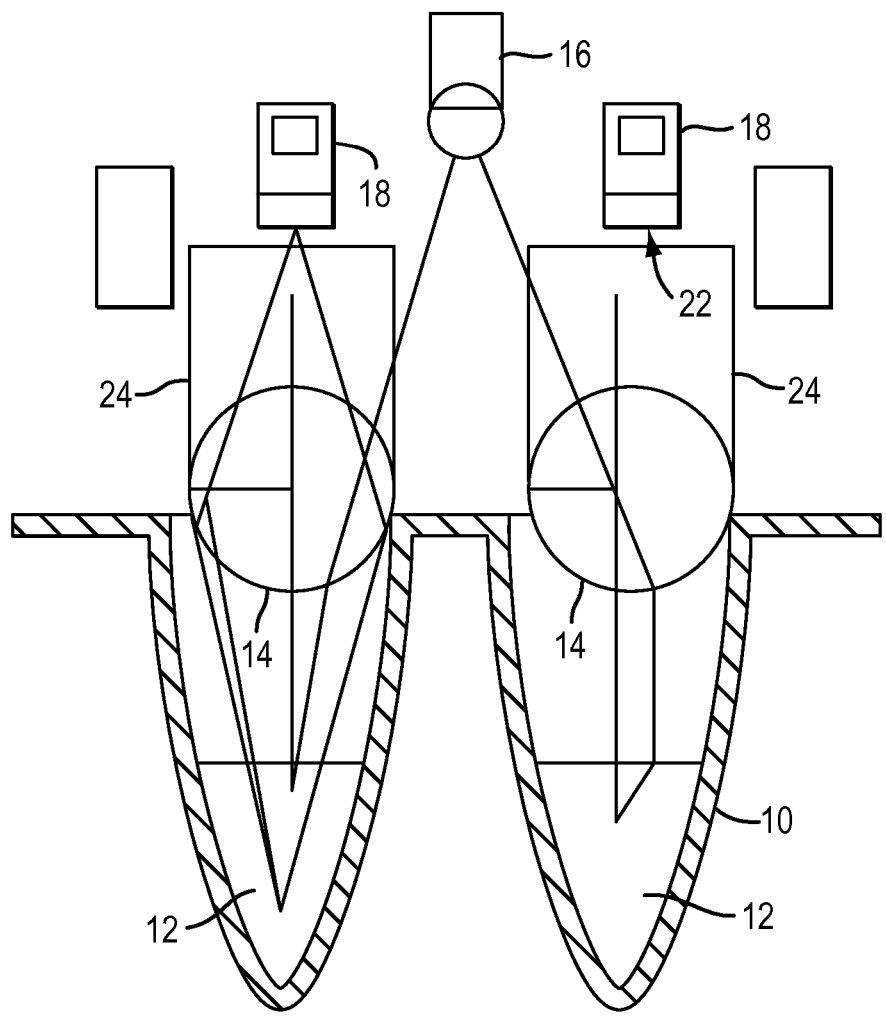
FIG. 7 depicts various embodiments having one light source emitting excitation wavelengths toward multiple sample wells, each well having a respective detector.

According to various embodiments, the excitation wavelength-excluding device can include multiple devices arranged in an array 36, as shown, for example, in FIG. 6c. According to various embodiments, the excitation wavelength-excluding device can be a prism 26 and can be positioned between the multiple emission detectors 28 and the sample 12 as shown, for example, in FIG. 4. According to various embodiments, the excitation wavelength-excluding device can be a filter. Any filter known in the art can be used, for example, a single bandpass or longpass filter.

According to various embodiments, an excitation wavelength-focusing device can be arranged to ensure that substantially only excitation wavelengths, for example, wavelengths less than about 600 nm, are impinged on the sample. The structure of these devices is as described for the excitation-wavelength excluding device. If the light source is sufficiently monochromatic, the excitation wavelength-focusing device can be omitted. According to various embodiments, the excitation wavelength-focusing device can be located between the detector and the sample well, between a detector and a lens, or between a lens and a sample well, for example.

According to various embodiments, a lightpipe 24 can be provided between the light source and the sample, and/or between the detector and the sample, as shown, for example, in FIGS. 1 and 6a. The lightpipe can be located between the light source or detector and a lens, according to various embodiments. The lightpipe 24 allows the generation of an excitation wavelength, and/or the detection of an emission wavelength, remotely from the sample well 10. The lightpipe 24 can be any suitable device for carrying wavelengths of light from one location to another without causing a significant loss of strength or shift in wavelength. According to various embodiments, such devices can include, for example, one or more fiber optic devices, mirrors, and/or lenses for transmitting the light to the sample from a remote location, and/or for transmitting the light from the sample to a remote location.

According to various embodiments, each individual light source can be provided with a light delivering light pipe 40. Each light delivery lightpipe 40 can remain separate between the light source or detector, and the sample, or each light delivery lightpipe from the light source or detector can converge to form a single lightpipe at the sample end of the lightpipe, as shown, for example, in FIG. 6a.

According to various embodiments, a method of differentiating multiple fluorescent signals by excitation wavelength can be provided. In the method, a sample 12 including a plurality of components is provided in a sample well 10. A plurality of fluorescent dyes is added to the sample 12. The plurality of fluorescent dyes can be chosen such that the emission of each fluorescent dye is greatly increased when a particular component is present in the sample 12. When the particular component is present in the sample 12, the dye can become unquenched.

Each of the plurality of detectable markers, for example, fluorescent dyes, can be selected to have an individual respective excitation wavelength or wavelength range. Each of the plurality of fluorescent dyes can be selected to possess an individual and respective emission wavelength or wavelength range. The emission wavelength or wavelength range can overlap with an emission wavelength or wavelength range of one or more of the other fluorescent dyes. A respective excitation wavelength or wavelength range is emitted from the light source 16 or 30, toward the sample 12 to fluoresce a fluorescent dye, for example, when the dye is in the presence of a target analyte in the sample 12. Emission wavelengths and wavelength ranges that are emitted from the sample 12 within the emission wavelength range of the plurality of fluorescent dyes, can be detected. The presence of a particular component in the sample 12 can be determined by the detected emission wavelength or wavelength range. The method can then be repeated utilizing different excitation wavelengths emitted from the light source 13 or 30 to determine the presence of other particular components in the sample 12.

According to various embodiments, the light source can be a Light Emitting Diode (LED). The LED can be, for example, an Organic Light Emitting Diode (OLED), a Thin Film Electroluminescent Device (TFELD), or a Quantum dot based inorganic "organic LED." The LED can include a phosphorescent OLED (PHOLED).

As used herein, the terms "excitation source" and "light source" are used interchangeably.

According to various embodiments, excitation beams emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as a focusing lens.

According to various embodiments, a light source can contain one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments wherein the LED or array of LEDs can emit, for example, at least about 50 mW of excitation energy, a cooling device such as, but not limited to, a heat sink or fan can be used with the LED. An array of high-powered LEDs can be used that draws, for example, about 10 watts of energy or less, about 10 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Exemplary LED array sources are available, for example, from Stocker Yale under the trade name LED AREALIGHTS. According to various embodiments, LED light sources can use about 1 microwatt of power or less, for example, about 1 mW, about 5 mW, about 25 mW, about 50 mW, about 1W, about 5W, about 50W, or about 100W or more, individually or when in used in an array.

According to various embodiments, a quantum dot can be used as a source for luminescence and as a fluorescent marker. The quantum dot based LED can be tuned to emit light in a tighter emission bandpass, thus the quantum dot based LED can increase the efficiency of the fluorescent system. Quantum dots can be molecular-scale optical beacons. The quantum dot nanocrystals can behave like molecular LEDs (light emitting diodes) by "lighting up" biological binding events with a broad palette of applied colors. Quantum dots can provide many more colors than conventional fluorophores. Quantum dots can possess many other very desirable optical properties. Nanocrystal quantum dots can be covalently linked to biomolecules using standard conjugation chemistry. The quantum dot conjugate can then be used to detect a binding partner in a wide range of assays. According to various embodiments, streptavidin can be attached to quantum dots to detect biotinylated molecules in a variety of assays. Quantum dots can also be attached to antibodies and oligonucleotides. Any assay that currently uses, for example, fluorescent-tagged molecules, calorimetric enzymes, or colloidal gold, can be improved with quantum dot nanocrystal-tagged conjugates. An exemplary quantum dot implementationis available from Quantum Dot Corporation of Haywood, Calif. under the trademark QDOT. More information about quantum dots and their applications can be found at, for example, www.qdot.com. U.S. Pat. Nos. 6,207,229, 6,251,303, 6,306, 310, 6,319,426, 6,322,901, 6,326,144, 6,426,513, and 6,444, 143 to Bawendi et al., U.S. Pat. Nos. 5,990,479, 6,207,392, and 6,423,551 to Weiss et al., U.S. Pat. No. 6,468,808 to Nie et al., and U.S. Pat. Nos. 6,274,323 to Bruchez et al., describe a variety of biological applications, methods of quantum dot manufacturing, and apparatuses for quantum dot nanocrystals and conjugates, all of which are incorporated herein by reference in their entireties.

Quantum dots can provide a versatile probe that can be used in, for example, in multiplex assays. Fluorescent techniques using quantum dot nanocrystals can be much faster than conventional enzymatic and chemiluminescent techniques, can reduce instrument tie-up, and can improve assay throughput. Colorimetric or detected reflectance techniques can be inferior to fluorescence and difficulties ensue when multiplex assays are developed based on these materials. Quantum dots can absorb all wavelengths "bluer" (i.e., shorter) than the emission wavelength. This capability can simplify the instrumentation required for multiplexed assays, since all different label colors can be excited with a single excitation source.

A Quantum dot based LED can emit light in an emission band that is narrower than an emission band of a normal LED, for example, about 50% narrower or about 25% narrower. The Quantum dot based LED can also emit light at an electrical energy conversion efficiency of about, 90% or more, for example, approaching 100%. OLED films, including Quantum dot based LEDs, can be applied to a thermal block, used for heating and cooling samples, in a fluorescence system without interfering with the operation of the thermal block.

According to various embodiments, when an OLED is used, the OLED can have any of a variety of sizes, shapes, wavelengths, or combinations thereof. The OLED can provide luminescence over a large area, for example, to luminescence multiple sample wells. Scatter or cross-talk light between multiple sample wells for this single OLED can be reduced by either overlaying a mask on the OLED or by patterning the luminescent in the OLED to operatively align with the multiple sample wells. The OLED can be a low power consumption device. Examples of OLEDs in various configurations and wavelengths are described in, for example, U.S. Pat. No. 6,331,438 B1, which is incorporated herein by reference in its entirety. The OLED can include a small-molecule OLED and/or a polymer-based OLED also known as a Light-Emitting Polymer (LEP). A small-molecule OLED that is deposited on a substrate can be used. An OLED that is deposited on a surface by vapor-deposition technique can be used. An OLED can be deposited on a surface by, for example, silk-screening. An LEP can be used that is deposited by, for example, solvent coating.

According to various embodiments, an OLED is used and can be formed from one or more stable, organic materials. The OLED can include one or more carbon-based thin films and the OLED can be capable of emitting light of various colors when a voltage is applied across the one or more carbon-based thin films.

According to various embodiments, the OLED can include a film that is located between two electrodes. The electrodes can be, for example, a transparent anode, a metallic cathode, or combinations thereof. Several separate emission areas can be stimulated between a single set of electrodes where simultaneous illumination of the separate emission areas is required. According to such embodiments, only one power and control module might be required for several apparent light sources. The OLED film can include one or more of a hole-injection layer, a hole-transport layer, an emissive layer, and an electron-transport layer. The OLED can include a film that is about one micrometer in thickness, or less. When an appropriate voltage is applied to the film, the injected positive and negative charges can recombine in the emissive layer to produce light by means of electroluminescence. The amount of light emitted by the OLED can be related to the voltage applied through the electrodes to the thin film of the OLED. Various materials suitable for fabrication of OLEDs are available, for example, from H. W. Sands Corp. of Jupiter, Fla.

Various types of OLEDs are described, for example, in U.S. Pat. No. 4,356,429 to Tang, U.S. Pat. No. 5,554,450 to Shi et al., and U.S. Pat. No. 5,593,788 to Shi et al., all of which are incorporated herein by reference in their entireties.

According to various embodiments, an OLED can be used and produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement. One or more OLEDs can form a shape surrounding, for example, a sample reservoir, a series of sample reservoirs, an array of a plurality of sample reservoirs, or a sample flow path. The sample path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, one or more excitation filters can be incorporated into the OLED substrate, thus eliminating additional equipment and reducing the amount of space needed for an optical system. For example, one or more filters can be formed in a layer of a substrate including one or more OLEDs and a layer including a sample flow path. The wavelength emitted by the OLED can be tuned by printing a fluorescent dye in the OLED substrate, as taught, for example, by Hebner et al. in "Local Tuning of Organic Light-Emitting Diode Color by Dye Droplet Application," APPLIED PHYSICS LETTERS, Vol. 73, No. 13 (Sep. 28, 1998), which is incorporated herein by reference in its entirety. When using multiple emission lines in an OLED, the OLED can be used in combination with a multiple notch emission filter.

According to various embodiments, an OLED can be substituted in place of any of the systems, devices, or apparatuses where an LED is shown. The OLED light source can have several OLED films stacked and operatively disposed such that several wavelengths of excitation beams can traverse the same optical path to illuminate the sample well. Several OLEDs forming excitation beams of the same wavelength can be stacked to provide higher output to illuminate the sample well.

According to various embodiments, a sample well can be placed in between an excitation source and a detector. The sample well can be a micro card, for example, a microtiter card, such as a 96-well microtiter card. The excitation source can be, for example, an OLED, standard LED, or combination thereof.

According to various embodiments, the light source can be a Solid State Laser (SSL) or a micro-wire laser. The SSL can produce monochromatic, coherent, directional light and can provide a narrow wavelength of excitation energy. The SSL can use a lasing material that is distributed in a solid matrix, in contrast to other lasers that use a gas, dye, or semiconductor for the lasing source material. Examples of solid state lasing materials and corresponding emission wavelengths can include, for example: Ruby at about 694 nm; Nd:Yag at about 1064 nm; Nd:YVO4 at about 1064 nm and/or about 1340 nm and which can be doubled to emit at about 532 nm or about 670 nm; Alexandrite at from about 655 nm to about 815 nm; and Ti:Sapphire at from about 840 nm to about 1100 nm. Micro-wire lasers are lasers where the wavelength of an excitation beam formed by the laser can be tuned or adjusted by altering the size of a wire. According to various embodiments, other solid state lasers known to those skilled in the art can also be used, for example, laser diodes. The appropriate lasing material can be selected based on the fluorescing dyes used, the excitation wavelength required, or both.

If a SSL is used, the laser can be selected to closely match the excitation wavelength of a fluorescent dye. The operating temperature of the system can be considered in selecting an appropriate SSL. The operating temperature can be regulated or controlled to change the emitted wavelength of the SSL. The light source for the laser can be any source as known to those skilled in the art, such as, for example, a flash lamp. Useful information about various solid state lasers can be found at, for example, www.repairfaq.org/sam/lasersl.htm. Examples of solid state lasers used in various systems for identification of biological materials can be found in, for example, U.S. Pat. No. 5,863,502 to Southgate et al. and U.S. Pat. No. 6,529,275 B2 to Amirkhanian et al.; both of which are incorporated herein by reference in their entireties.

According to various embodiments, various types of light sources can be used singularly or in combination with other light sources. One or more OLEDs can be used with, for example, one or more non-organic LEDs, one or more solid state lasers, one or more halogen light sources, or combinations thereof.

According to various embodiments, a light source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, or combinations thereof.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light sources and a sample. One or more emission filters can be associated with an emission beam from an excited dye. One or more filters can be located between the sample and one or more emission beam detectors.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with one or more light sources to form at least one excitation beam. One or more filters can be located between the one or more light sources and a sample. One or more emission filters can be associated with an emission beam from an excited dye. One or more filters can be located between the sample and one or more emission beam detectors.

According to various embodiments, a filter can be a single bandpass filter or a multiple bandpass filter. As used herein, a bandpass filter and a passband filter are used interchangeably. A multiple passband filter can be, for example, a multiple-notch filter or a multi-rugate filter. A multiple passband filter can be used with an incoherent light source, for example, a halogen lamp, a white light source, and/or one or more LEDs or OLEDs emitting light at different wavelengths. A multiple passband filter can be used with a multiple laser-based light source emitting light at different wavelengths. Examples of manufacturing and use of rugate filters and rugate beam splitters can be found in, for example, U.S. Pat. No. 5,863,502 to Southwell, U.S. Pat. No. 6,256,148 to Gasworth, and U.S. Pat. No. 6,529,275 B2 to Rahmlow, Jr., all of which are incorporated herein by reference in their entireties.

According to various embodiments, a multiple passband filter can be used with a dichroic beam splitter, a 50/50 beam splitter, a dichroic beam splitter that has several "passbands," or no beam splitter. A multiple beam splitter can be coated at an angle, causing a variance in a thickness across a filter substrate, to compensate for wavelength shift with an angle. A multiple passband filter can be formed by coating different light interference materials over respective areas of a substrate used in a multiple passband filter manufacture.

A Rugate filter is an example of an interference coating based on the refractive index that varies continuously in a direction, for example, perpendicular or 45 degrees to the film plane. When the refractive index varies periodically within two extreme values, a minus filter with high transmittance on either side of the rejection band can be made. Periodic Rugate filters can be manufactured.

Rugate notch filters can use refractory metal oxides to achieve coatings with exceptional thermal and environmental stability. These filters can be used in place of other types of notch filters, particularly where durability and reliability are desired. Rugate notch filters are available from Barr Associates (Westford, Mass.). The Rugate notch filter can be used as edge filters and beam splitters. Filter sizes or shapes are not limitations for the rugate notch filter. The rugate notch filter can provide environmental and thermal stability, a broad operating temperature range, narrow rejection bands, variety of shapes & sizes, high throughput, low ripple, and/or a broad spectral range. More information is available from, for example, www.barr-associates-uk.com, www.barrassociates.com/opticalfilters.php.

Multiple-notch filters can be made, for example, with a measured blocking of O.D. 6 or better. Notch filters with this type of deep blocking level at the light wavelength can also afford high transmission close to the light line.

According to various embodiments, excitation levels can increase when multiple dyes spaced apart spectrally are irradiated with excitation beams. This can lead to less spectral crosstalk. The dye matrix, condition number, and/or deconvolution in a system can be improved. The increased excitation levels can provide higher signal levels. Higher signal levels can be seen during the utilization of dyes that emit in the "red" spectrum. The dynamic range of the system can be improved. The system can reduce the compensation for variation in the emission beam intensity for various dyes.

According to various embodiments, the multiple dyes can be deposited in a sample well using a fluid transfer technique, such as, for example, manual pipette, robotic pipette, or injection. According to various embodiments, the multiple dyes can be deposited in a sample well, for example, by ink-jet spraying, as beads, or as a mixture of a plurality of dyes.

Figure 9:
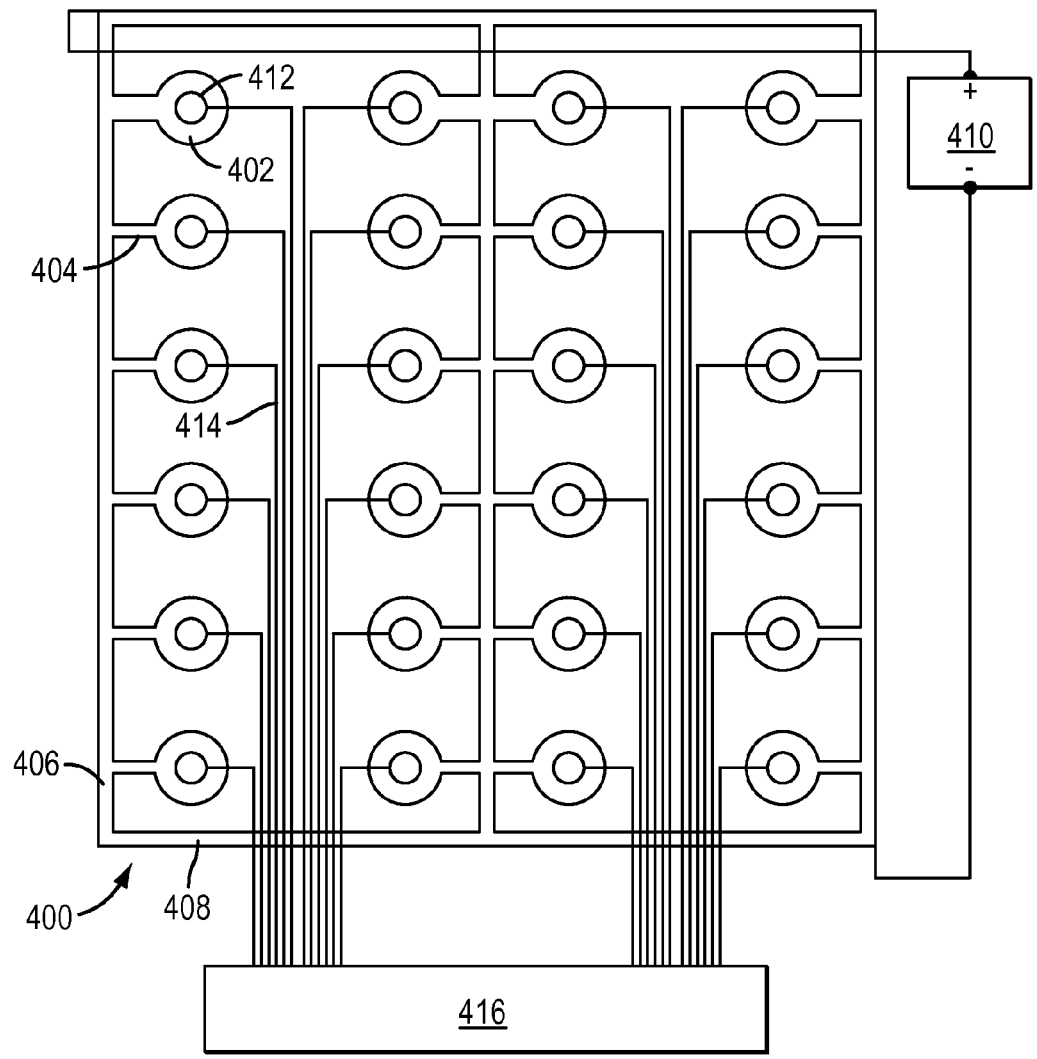
FIG. 9 illustrates an exemplary embodiment of a light source layout, for example, an organic light emitting diode (OLED) layout.

FIG. 9 is a bottom view that illustrates an OLED layout 400 that can be used as a light source, together with a plurality of photodiode detectors 412, according to various embodiments. The OLED layout 400 can include a plurality of OLED well lamps 402, each positioned, when in operation, above a respective well of a multi-well sample well array. Each OLED material well lamp 402 can be connected to, or integrally formed with, a respective connection arm 404 that leads to a layout terminal 406. Each layout terminal can be connected to or integrally formed with the respective connection arms 404 branching from the layout terminal.

The connection arms 404 branch off of side terminals 406 and 408. The OLED layout can be connected to respective opposite electrical connections, for example, opposite terminals of a power supply. The OLED layout can be connected to the power supply through leads arranged at opposite corners of the OLED layout. The power supply can include or be connected to one or more of a switch, a meter, an oscillator, a potentiometer, a detector, a signal processing unit, or the like. Alternatively, or additionally, connection arms 404 can each include a wire or electrical lead in the form of, for example, a metal wire. The OLED layout can include a plurality of individually addressable OLED lighting elements (not shown) with a separate lead connected to each lighting element. The wiring, leads, terminals, connection arms, and the like can be implemented in, for example, a substrate or a film. An OLED layout control unit 410 can be used to supply power and control the OLED layout 400. A plurality of detectors 412 can be electrically connected to a detector control unit 416 through respective detector leads 414 as shown.

The plurality of detectors can be arranged, for example, centered, on the plurality of OLED well lamps 402, on the sides of well lamps that face respective sample wells, and/or when operatively positioned adjacent a multi-well sample well array. The detectors can be configured to detect light emitted from the sample wells of a sample well array, without being flooded or bleached out by the respective OLED well lamps. For example, a mask material can be disposed between the detectors and the respective OLED well lamps. The detector 412 can be formed in the same substrate as the OLED lamp.

The exemplary OLED layout shown in FIG. 9 is shaped to be aligned with a 24 well sample well array. Other embodiments of OLED layouts using various shapes and various numbers of well lamps are within the scope of the present teachings.

According to various embodiments, each well lamp 402 can include, for example, four individual lamps or OLED layers, capable of producing excitation wavelengths at four different frequencies.

The OLED layout can be constructed of a unitary or multipart construction, of molded material, of stamped material, of screen printed material, of cut material, or the like.

Figure 10:
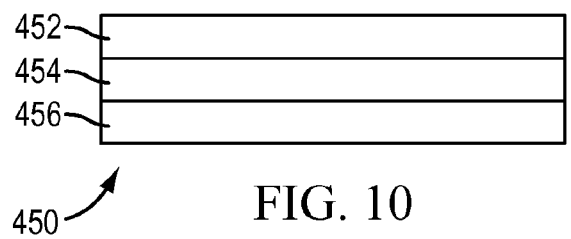
FIG. 10 illustrates an exemplary embodiment of a light source layout, for example, an OLED layout with varying color OLEDs stacked upon each other.

FIG. 10 illustrates an exemplary embodiment of a light source layout. An OLED layout 450 can include varying color OLEDs 452, 454, and 456 stacked upon each other. The layout can be useful for a compact light source design capable of forming excitation beams at varying wavelengths. The OLEDs 452, 454, and 456 can be transparent, allowing excitation beams from each OLED to pass through any other OLED so as to be directed towards a sample. The OLEDs 452, 454, and 456 can emit different colors, same colors, or a combination thereof depending on the color intensity and variety required. The OLEDs 452, 454, and 456 can share an electrode, for example, a cathode. One electrode, for example, an anode, for powering each of the OLEDs 452, 454, and 456 can be connected in electrical isolation from each respective anode to a control unit (not shown) if the capability to independently activate each of the OLEDs 452, 454, and 456 is desired. The OLEDs 452, 454, and 456 can electrically share one electrode, two electrodes, or no electrodes. Any number of OLEDs can be stacked, for example, two OLEDs, three OLEDs, four OLEDs, or more OLEDs, to form a light source, a respective light source, or an array of light sources.

According to various embodiments, multiple excitation wavelengths can be used to detect multiple sample components. According to various embodiments, the apparatus and method can be adapted for use by any suitable fluorescence detection system. For example, various embodiments of the apparatus and method can be used in a sequencing system with single or multiple samples, for example, in a nucleic acid sequence amplification reaction, in a sequencing detection system.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed is:

1. An apparatus comprising:
   a thermal cycler;
   a plurality of reaction regions, each comprising a respective sample disposed therein, the plurality of reaction regions being connected to the thermal cycler, the thermal cycler being adapted to carry out thermal cycling to effect a polymerase chain reaction on the respective samples in the plurality of reaction regions;
   a plurality of detectors disposed above the samples and capable of detecting emission beams emitted from the plurality of reaction regions, the plurality of detectors including a different detector centered above each one of the reaction regions;
   for each detector, four or more excitation light sources capable of providing a plurality of separate excitation beams, each excitation beam comprising a wavelength range that is not provided by the other excitation beams of the plurality of separate excitation beams, each excitation light source being capable of directing a respective excitation beam along a beam path toward the respective reaction region, the four or more excitation light sources for each detector surrounding the respective detector and being spaced above the respective sample disposed in the reaction region;
   a control unit capable of activating each of the four or more excitation light sources for each detector independently from the other excitation light sources of the respective four or more excitation light sources; and
   a detection system configured to control the plurality of detectors to simultaneously detect emission beams from each of the plurality of reaction regions and to associate the emission beams detected from each of the plurality of reaction regions with the excitation light source activated by the control unit.

2. The apparatus of claim 1, wherein each of the plurality of detectors is capable of comparing each excitation beam with a detected signal to determine the presence or absence of a component.

3. The apparatus of claim 1, wherein the control unit is capable of storing in memory the wavelength of each of the separate excitation beams and respective detection signals resulting from illuminating the samples in the plurality of reaction regions with the excitation beams.

4. The apparatus of claim 1, wherein the control unit is capable of comparing a detection signal with a preset value and, based on that comparison, determining a presence or an absence of a component in one of the samples.

5. The apparatus of claim 1, wherein the four or more excitation light sources for each detector comprise at least one of a light emitting diode, an organic light emitting diode, a semiconductor laser, and a solid state laser.

6. The apparatus of claim 1, wherein each sample comprises a plurality of components and a plurality of detectable markers, each of the plurality of detectable markers being capable of generating increased emission due to a presence of a target component in the sample, each of the plurality of detectable markers having a respective excitation wavelength range and a respective emission wavelength range, and each of the four or more light sources is capable of independently emitting a plurality of excitation wavelength ranges toward the sample to respectively excite a respective one of the detectable markers, each of the plurality of excitation wavelength ranges corresponding to a respective excitation wavelength range of a respective one of the plurality of detectable markers.

7. The apparatus of claim 6, wherein the four or more light sources are capable of sequentially emitting a plurality of excitation wavelength ranges toward the sample and each of the plurality of detectors is capable of sequentially detecting whether a corresponding emission wavelength range is emitted from the sample.

8. The apparatus of claim 6, further comprising a lens arranged to receive the plurality of excitation wavelengths emitted from the four or more light sources for each detector and to receive emission wavelengths emitted from the sample.

9. The apparatus of claim 8, wherein the lens is a focusing lens.

10. The apparatus of claim 8, wherein the lens is a Fresnel lens or a prism.

11. The apparatus of claim 8, wherein the four or more light sources for each detector comprises, a light emitting diode, an organic light emitting diode, a laser, a solid state laser, or a combination thereof.

12. The apparatus of claim 6, wherein the four or more light sources for each detector comprises an array of light generating sources.

13. The apparatus of claim 12, wherein the array of light generating sources includes an array of light emitting diodes.

14. The apparatus of claim 12, wherein the array of light generating sources includes an organic light emitting diode layout.

15. The apparatus of claim 12, wherein the array of light generating sources comprises one or more light emitting diodes.

16. The apparatus of claim 12, wherein the array of light generating sources includes one or more lasers.

17. The apparatus of claim 12, wherein the array of light generating sources includes a solid state laser.

18. The apparatus of claim 6, further comprising a lightpipe arranged between the light source and the sample.

19. The apparatus of claim 6, further comprising a lightpipe arranged between the detector and the sample.

20. The apparatus of claim 6, further comprising an excitation wavelength-excluding device arranged between the sample and the detector.

21. The apparatus of claim 20, wherein the excitation wavelength-excluding device comprises a longpass filter, a multiple notch filter, a bandpass filter, or a combination thereof.

22. The apparatus of claim 6, further comprising an excitation wavelength-excluding device arranged between the light source and the sample.

23. The apparatus of claim 22, wherein the excitation wavelength-excluding device comprises a longpass filter, a multiple notch filter, a bandpass filter, or a combination thereof.

24. The apparatus of claim 6, further comprising a mirror arranged between both the light source and the sample, and the detector and the sample.

25. The apparatus of claim 1, wherein the excitation light source is spaced above the respective sample disposed in the reaction region in a range of from D/2 to 5D from a top surface of the sample, where D is the depth of the sample in the reaction region.

26. A method comprising:
    providing a set of samples that includes at least two detectable markers, wherein each detectable marker emits a respective detectable emission beam when illuminated by an excitation beam that includes light of a respective wavelength;
    thermally cycling the set of samples to perform a polymerase chain reaction;
    illuminating the set of samples with a first excitation beam, directed from a first excitation light source disposed above the samples, that includes a first excitation wavelength, during the thermal cycling;
    simultaneously detecting first emission beams emitted from the set of samples, with a plurality of detectors including a different detector centered above each one of the samples, in response to illuminating the set of samples with the first excitation beam, during the thermal cycling, wherein the first emission beams include a first emission wavelength emitted from at least one sample of the set of samples;
    independently illuminating the set of samples with a second excitation beam, that differs from the first excitation beam, directed from a second excitation light source disposed above the samples, that includes a second excitation wavelength that differs from the first excitation wavelength, and that does not include the first excitation wavelength, during the thermal cycling; and
    simultaneously detecting second emission beams emitted from the set of samples with the plurality of detectors in response to illuminating the set of samples with the second excitation beam, during the thermal cycling, wherein the second emission beams include the first emission wavelength emitted from at least one sample of the set of samples.

27. The method of claim 26, wherein the at least two detectable markers comprise fluorescent dyes.

28. The method of claim 26, wherein the sample includes at least four detectable markers and the method comprises illuminating with at least four different excitation beams.

29. The method of claim 26, wherein the excitation light source is spaced above the respective sample in a range of from D/2 to 5D from a top surface of the sample, where D is the depth of the sample.

30. A method of differentiating multiple fluorescent signals by excitation wavelength, comprising:
    (a) providing a respective sample in each of a plurality of sample wells, each sample comprising a plurality of components;
    (b) adding four or more fluorescent dyes to each sample, each of the four or more fluorescent dyes being capable of generating increased emission due to a presence of a respective target component in the sample, each of the four or more fluorescent dyes possessing a respective excitation wavelength range and a respective emission wavelength range;
    (c) thermally cycling each sample to perform a polymerase chain reaction;
    (d) directing beams of at least four different excitation wavelength ranges from a different light source disposed above each respective sample toward the sample to cause at least a respective four of the fluorescent dyes to emit a detectable emission, during the thermal cycling;
    (e) simultaneously detecting emission beams emitted from each sample with a plurality of detectors including a different detector centered above each respective sample, during the thermal cycling; and
    (f) determining whether each of four respective target components is present in the sample by analyzing the detected emission wavelengths.

31. The method of claim 30, further comprising passing at least one of the beams of the at least four different excitation wavelength ranges, and the emission beams, through a lens.

32. The method of claim 30, further comprising passing the emission beams through a filter before the detecting.

33. The method of claim 31, wherein the method comprises subjecting the sample to nucleic acid sequence amplification.

34. The method of claim 31, wherein the nucleic acid sequence amplification comprises polymerase chain reaction.

35. The method of claim 30, wherein the light source is spaced above the sample in a range of from D/2 to 5D from a top surface of the sample in the sample well, where D is the depth of the sample in the sample well.

36. An analytical instrument comprising:
    a thermal cycler;
    a plurality of reaction regions, each comprising a respective sample disposed therein, the plurality of reaction regions being connected to the thermal cycler, the thermal cycler being adapted to carry out thermal cycling to effect a polymerase chain reaction on the respective samples in the plurality of reaction regions;
    at least one excitation beam source array comprising a plurality of light sources comprising four or more excitation beam source portions and including a different light source disposed above each respective one of the plurality of samples, the four or more excitation beam source portions being controllable to emit at least four different excitation wavelengths;
    a control unit capable of activating each of the four or more excitation beam source portions independently from the others of the four or more excitation beam source portions;
    at least one detector array comprising a plurality of detector portions including a different detector portion spaced above and centered above each respective one of the samples; and
    a detector system configured to control the detector array to simultaneously detect emission beams from each of the plurality of reaction regions and to associate the emission beams detected from each of the plurality of detection regions with the excitation beam source portion activated by the control unit;
    wherein at least one of the plurality of the excitation beam source portions is arranged between two of the plurality of detector portions, at least one of the plurality of detector portions is arranged between two of the plurality of excitation beam source portions, and each of the at least four different excitation wavelengths emitted from the four or more excitations beam source portions is divided to provide excitation beams to two or more of the plurality of reaction regions.

37. The analytical instrument of claim 36, wherein at least one of the plurality of the detector portions is arranged laterally or longitudinally adjacent two of the four or more excitation beam source portions.

38. The analytical instrument of claim 36, wherein the at least one excitation beam source array has openings therein and the plurality of detector portions are aligned to detect emissions beams that travel through the openings of the at least one excitation beam source array.

39. The analytical instrument of claim 36, wherein the at least one detector array has openings therein and the four or more excitation beam source portions of the at least one excitation beam source array are aligned to transmit through the openings of the at least one detector array.

40. The analytical instrument of claim 36, wherein the at least one excitation beam source array and the at least one detector array are in contact with each other.

41. The analytical instrument of claim 36, wherein each of the four or more excitation beam source portions comprise at least one of a light emitting diode, an organic light emitting diode, a quantum dot, and a solid state laser.

42. The analytical instrument of claim 36, further comprising a focusing array comprising a plurality of focusing portions, wherein each of the plurality of focusing portions is disposed adjacent one respective excitation beam source portion of the four or more excitation beam source portions.

43. The analytical instrument of claim 42, wherein the focusing array further comprises a plurality of second focusing portions, wherein each of the plurality of second focusing portions is disposed adjacent one respective detector portion of the plurality of detector portions.

44. The analytical instrument of claim 36, further comprising a focusing array including a plurality of focusing portions, wherein each of the plurality of focusing portions is disposed adjacent one respective detector portion of the plurality of detector portions.

45. The analytical instrument of claim 36, wherein the at least one detector array comprises at least one of a camera, a charge-coupled detector, a photodiode, a photomultiplier, a complimentary metal-oxide semiconductor, and a combination thereof.

46. The analytical instrument of claim 36, wherein the excitation beam source array is spaced above the sample in a range of from D/2 to 5D from a top surface of the sample, where D is the depth of the sample.

47. A system comprising:
an analytical instrument including a plurality of reaction regions, each region comprising a respective sample disposed therein, the plurality of reaction regions being connected to a thermal cycler, the thermal cycler being adapted to carry out thermal cycling to effect a polymerase chain reaction on the respective samples in the plurality of reaction regions;
at least one excitation beam source array comprising a plurality of light sources each comprising four or more excitation beam source portions, a different light source being disposed above each of the respective samples, the four or more excitation beam source portions being controllable to emit at least four different excitation on wavelengths;
at least one detector array comprising a plurality of detector portions including a different detector portion disposed above each of the respective samples;
a detector system configured to control the detector array to simultaneously detect emission beams from each of the plurality of reaction regions, wherein at least one of the four or more excitation beam source portions or at least one of the plurality of detector portions is arranged and centered between two of the other; and
a sample-containment component including a plurality of sample-containment units,
wherein each of the four or more excitation beam source portions is operatively aligned to direct excitation beams towards a different one of the sample-containment units, and each of the plurality of detector portions is centered above a different one of the plurality of sample-containment units.

48. The system of claim 47, further comprising a control device configured to activate at least some of the four or more excitation beam source portions.

49. The system of claim 47, wherein the plurality of sample-containment units comprises at least about 12 sample-containment units.

50. The system of claim 47, wherein the sample-containment component includes about 96 sample-containment units.

51. The system of claim 47, wherein at least one of the plurality of sample-containment units contains components for promoting a nucleic acid sequence amplification reaction.

52. The system of claim 51, wherein the nucleic acid sequence amplification reaction is a polymerase chain reaction and at least one of the plurality of sample-containment units contains a nucleic acid sequence amplification dye.

53. The system of claim 47, wherein the excitation beam source array is spaced above the sample disposed in the reaction region in a range of from D/2 to 5D from a top surface of the sample, where D is the depth of the sample in the reaction region.

54. A method of irradiating samples in sample-containment units, the method comprising:
providing a thermal cycler;
providing an analytical instrument comprising a plurality of reaction regions, each reaction region comprising a respective sample disposed therein, the plurality of reaction regions being connected to the thermal cycler, the thermal cycler being adapted to carry out thermal cycling to effect a polymerase chain reaction on the respective samples in the plurality of reaction regions, at least one excitation beam source array comprising a plurality of light sources, each light source comprising four or more excitation beam source portions and being disposed above a different one of the respective samples, at least one detector array including a plurality of detector portions including a different detector portion disposed above each of the respective samples in the plurality of reaction regions, and a detector system configured to control the detector array to simultaneously detect emission beams from each of the plurality of reaction regions, wherein at least one of the four or more excitation beam source portions or at least one of the plurality of detector portions is arranged and centered between two of the other;
thermally cycling the respective samples to effect a polymerase chain reaction;

generating at least four excitation beams having different excitation wavelengths with at least four of the four or more excitation beam source portions, during the thermal cycling; and directing the at least four excitation beams toward the respective samples.

55. The method of claim 54, further comprising simultaneously detecting emission beams emitted from the samples in the plurality of reaction regions, with the plurality of detector portions, and each of the plurality of detector portions is centered above a respective one of the plurality of reaction regions.

56. The method of claim 54, further comprising focusing at least one of the at least four generated excitation beams to form a focused excitation beam.

57. The method of claim 54, wherein each of the plurality of reaction regions are disposed within a respective one of a plurality of sample-containment units, and the method further comprises splitting at least one of the at least four excitation beams into two or more spaced-apart excitation beam portions; and directing the two or more spaced-apart excitation beam portions towards two or more respective sample-containment units.

58. The method of claim 54, further comprising passing at least one of the at least four generated excitation beams through an electromagnetic radiation filter.

59. The method of claim 55, further comprising passing the emission beams through an electromagnetic radiation filter.

60. The method of claim 55, further comprising generating a first data set representative of the detected emission beams.

61. The method of claim 54, wherein the sample comprises components capable of enabling a nucleic acid sequence amplification reaction.

62. The method of claim 54, wherein the sample comprises components capable of enabling a polymerase chain reaction.

63. The method of claim 54, wherein the excitation beam source array is spaced above the sample disposed in the reaction region in a range of from D/2 to 5D from a top surface of the sample, where D is the depth of the sample in the reaction region.

* * * * *